United States Patent [19]

Kasai

[11] Patent Number: 5,177,007
[45] Date of Patent: Jan. 5, 1993

[54] PROCESS FOR PRODUCING OPTICALLY ACTIVE R-(+)-2,3-DICHLORO-1-PROPANOL USING MICROORGANISM

[75] Inventor: Naoya Kasai, Amagasaki, Japan

[73] Assignee: Daiso Co., Ltd., Osaka, Japan

[21] Appl. No.: 623,555

[22] Filed: Dec. 7, 1990

[30] Foreign Application Priority Data

Dec. 8, 1989 [JP] Japan .................................. 1-319305
Dec. 8, 1989 [JP] Japan .................................. 1-319306

[51] Int. Cl.$^5$ .......................... C12P 17/02; C12P 7/04; C12R 1/05; C07P 41/00
[52] U.S. Cl. ..................................... 435/123; 435/157; 435/252.1; 435/250; 435/829
[58] Field of Search ................ 435/157, 280, 829, 123

[56] References Cited

U.S. PATENT DOCUMENTS 4,840,907  6/1989  Kasai et al. .......................... 435/157
4,962,031 10/1990  Yoshida et al. ..................... 435/280

FOREIGN PATENT DOCUMENTS 0207636  1/1987  European Pat. Off. .

OTHER PUBLICATIONS

Chemical Abstracts, vol. 107, No. 25, Dec. 21, 1987, Columbus, Ohio, US; Abstract No. 234845j, Naoya Kasai, et al.
Chemical Abstracts, vol. 105, No. 17, Oct. 27, 1986, Columbus, Ohio, US; Abstract No. 151578g, Naoya Kasai, et al.

Primary Examiner—Herbert J. Lilling
Attorney, Agent, or Firm—Sherman and Shalloway

[57] ABSTRACT

A process for producing optically active R-(+)-2,3-dichloro-1-propanol, which comprises cultivating an S-(−)-2,3-dichloro-1-propanol-assimilating strain belonging to the genus Alcaligenes in a culture medium containing racemate 2,3-dichloro-1-propanol, and recovering optical isomer R-(+)-2,3-dichloro-1-propanol from the culture broth and a pure culture of an S-(+)-dichloro-1-propanol-assimilating strain belonging to the genus Alcaligenes.

13 Claims, 1 Drawing Sheet

PROCESS FOR PRODUCING OPTICALLY ACTIVE R-(+)-2,3-DICHLORO-1-PROPANOL USING MICROORGANISM

DETAILED DESCRIPTION OF THE INVENTION

1. Industrially Applicable Field

This invention relates to a process for producing optically active R-(+)-2,3-dichloro-1-propanol by treatment of recemate 2,3-dichloro-1-propanol with a microorganism.

More specifically, this invention relates to a process for producing optically active R-(+)-2,3-dichloro-1-propanol, which comprises cultivating a S-(-)-2,3-dichloro-1-propanol-assimilating strain belonging to the genus Alcaligenes in a culture medium containing racemate 2,3-dichloro-1-propanol, and recovering optical isomer R-(+)-2,3-dichloro-1-propanol from the culture broth.

This invention also pertains to a process for producing optically active S-(+)-epichlorohydrin, which comprises reacting the optical isomer R-(+)-2,3-dichloro-1-propanol obtained by the above process with alkali.

This invention further relates to a pure culture of a S-(-)-2,3-dichloro-1-propanol-assimilating strain belonging to the genus Alcaligenes, especially the genus Alcaligenes named DS-K-S38, which is suitable for use in the above process.

2. Prior Art 2,3-Dichloro-1-propanol (hereinafter, this compound is sometimes abbreviated as "β-DCH") is a compound represented by the following structural formula (I)

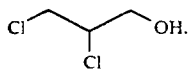

(I)

and its optically active β-DCH is an extremely valuable compound as an intermediate of various pharmaceuticals and pesticides, as is the case with optically active epichlorohydrin.

Synthesis of optically active epichlorohydrin is known and described, for example, in J. Org. Chem., vol. 43, page 4876, 1978 (Baldwin et al.), and J. Chem. Soc., Chem. Commun., page 1600, 1984 (Ellis et al.). The conventional synthesis methods, however, have the disadvantage of requiring highly sophisticated synthetic techniques, and no method has been known which can synthesize optically active epichlorohydrin having a high optical purity by a simple procedure.

Further, as a process to obtain optically active β-DCH, there has been known a process of separating the desired optically active isomer from racemate β-DCH, for example, a process which comprises acetylating the hydroxyl group of β-DCH with acetic anhydride and then making lipase act on the resulting 1-acetoxy-2,3-dichloropropane (Agric. Biol. Chem. 46(6), 1593–1597, 1982), or a process which comprises making lipase act on 2,3-dichloro-1-propanol and tributyrim to carry out stereospecific esterification (J. Am. Chem. Soc., 1984, 106, 2687–2692), but any of these processes only affords optically active 2,3-dichloro-1-propanol or its ester having low optical purity.

On the other hand, the present inventor has already proposed, together with another inventor, "A process for producing optically active dichloropropanol, which comprises cultivating and R-(+)-2,3-dichloro-propanol-assimilating strain belonging to the genus Pseudomonas in a culture medium containing racemate 2,3-dichloro-1-propanol, and recovering optically isomer S-(-)-2,3-dichloro-1-propanol from the culture broth, and a process for producing optically active epichlorohydrin, which comprises reacting the optical isomer S-(-)-2,3-dichloro-1-propanol obtained by the aforesaid process with an alkali."

According to the above proposed process, highly pure optically active S-(-)-β-DCH can readily be obtained.

Problems to be solved by the Invention

However, there has hitherto been known no convenient process to obtain the opposite optical isomer to the desired product of the above proposed process, namely, R-(+)-β-DCH. Especially, a process to obtain highly pure R-(+)-β-DCH using a microorganism has hitherto not been known at all.

Means for Solving the Problems

As a result of vigorous study on a process for obtaining highly pure R-(+)-β-DCH using a microorganism, the present inventor found that a certain kind of microorganisms, namely the genus Alcaligenes have an ability to assimilate S-(-)-β-DCH.

Thus, according to the invention is provided a process for producing optically active R-(+)-2,3-dichloro-1-propanol, which comprises cultivating an S-(-)-2,3-dichloro-1-propanol-assimilating strain belonging to the genus Alcaligenes in a culture medium containing racemate 2,3-dichloro-1-propanol, and recovering optical isomer R-(+)-2,3-dichloro-1-propanol from the culture broth.

As far as the present inventor knows, there has hitherto never been known the genus Alcaligenes having a property to assimilate S-(-)-2,3-dichloro-1-propanol.

The bacteriological characteristics of the microorganism which was newly separated and recovered from the soil by the present inventor and is capable of assimilating S-(-)-2,3-dichloro-1-propanol are set forth below in Table 1.

TABLE 1

| A. | Morphology | |
|---|---|---|
| | (1) | Shape and size of cells: rods: 0.4–0.6 × 1.8–2.2 μm |
| | (2) | Pleomorphisms of cells: none |
| | (3) | Mobility: +, peritrichous flagella |
| | (4) | Spores: none |
| | (5) | Gram strain: negative |
| | (6) | Acid fastness: none |
| B. | Cultural characteristics | |
| | (1) | Plate culture on nutrient agar (for 3 days at 30° C.) |
| | | (a) Speed of colony growth: Ordinary, about 3–4 mm in diameter |
| | | (b) Shape of colonies: circular |
| | | (c) Shape of colony surface: smooth |
| | | (d) Raised condition of colonies: convex |
| | | (e) Periphery of colonies: entire |
| | | (f) Contents of colonies: nomogeneous |
| | | (g) Color of colonies: milky white |
| | | (h) Transparency of colonies: translucent |
| | | (i) Gloss of colonies: dull |
| | | (j) Formation of soluble pigments: none |
| | (2) | Slant culture of nutrient agar (for 3 days at 30° C.) |
| | | (a) Growth: good, filiform |
| | | (b) Shape of colonies: smooth |
| | | (c) Raised condition of colonies in section: flat |

TABLE 1-continued

| | | |
|---|---|---|
| | (d) | Gloss of colonies: dull |
| | (e) | Shape of colony surface: smooth |
| | (f) | Transparency of colonies: translucent |
| | (g) | Color of colonies: milky white |
| (3) | Nutrient liquid culture (for 3 days at 30° C.) | |
| | (a) | Growth: Pellicular |
| | (b) | Turbidity: slightly turbid |
| | (c) | Gas production: none |
| | (d) | Coloration of the medium: none |
| (4) | Stab culture of nutrient gelatin | |
| | No liquefaction of gelatin | |
| (5) | Litmus milk | |
| | No change | |
| C. | Physiological characteristics | |
| | (Symbols: +, positive; −, negative) | |
| 1. | Reduction of nitrate: + | |
| 2. | MR test: − | |
| 3. | VP test: − | |
| 4. | Indole production: − | |
| 5. | Formation of hydrogen sulfide: − | |
| 6. | Hydrolysis of starch: − | |
| 7. | Denitrification: − | |
| 8. | Utilization of citric acid: + | |
| 9. | Utilization of inorganic nitrogen sources: + | |
| 10. | Formation of pigments: not particularly formed | |
| 11. | Urease: − | |
| 12. | Oxidase: + | |
| 13. | Catalase: + | |
| 14. | Growth range: pH 5.0–9.0; temperature 20–45° C. | |
| 15. | Aerobiosis: aerobic | |
| 16. | O-F test (Hugh Leifson method): 0 | |
| 17. | Formation of acids and gases from sugars | |

| Sugar | Acid | Gas |
|---|---|---|
| (1) D-glucose | − | − |
| (2) D-galactose | − | − |
| (3) sucrose | − | − |
| (4) trehalose | − | − |
| (5) starch | − | − |
| (6) glycerol | ± | − |

| | | |
|---|---|---|
| 18. | Arginine dihydrolase: − | |
| 19. | Accumulation of PHB: + | |

Assignment identification of the strain was carried out based on the above results according to Bergey's Manual of Systematic Bacteriology Vol. 1, and thereby it was revealed that the strain has the characteristics of the genus Alcaligenes. Thus, the present inventor named this strain Alcaligenes sp. DS-K-S38 (hereinafter, this strain is referred to as DS-K-S38 strain). This strain was deposited with Fermentation Research Institute, Agency of Industrial Science and Technology, Japan under deposit number of FERM P-11114 on Nov. 15, 1989.

The control of the above strain was, thereafter, transferred in the above Fermentation Research Institute in accordance with Budapest Treaty on the international recognition of the deposit of microorganism for the purpose of patent procedure, and the strain has been accepted under deposit number of FERM BP-3101.

In the invention, not to speak of the above DS-K-S38 strain and its variants and mutants, any bacterium can be used so long as it belongs to the genus Alcaligenes and has an ability to assimilate S-(-)-2,3-dichloro-1-propanol.

In the invention, optical resolution of the above racemate β-DCH is carried out by the above bacterium. In the invention, the above bacterium or its culture cells can be used as it is or after immobilization, and the cultivation method and immobilization of the bacterium may be a usually used method. Namely, as for the cultivation method, the above bacterium is cultivated in an nutrient medium containing carbon source(s), nitrogen source(s), organic nutrient source(s) and inorganic nutrient source(s), for example, a bouillon medium or a sugar-containing bouillon medium to abundant growth, and the cultivation product or culture cells obtained therefrom is used.

According to the process of this invention, the S-(-)-2,3-dichloro-1-propanol-assimilting strain belonging to the genus Alcaligenes is cultivated in a culture medium containing racemate 2,3-dichloro-1-propanol. The culture medium may contain other carbon sources in addition to the 2,3-dichloro-1-propanol, and further nitrogen sources and minerals. In one preferred embodiment, the culture medium may further contain one or more other carbon sources, one or more nitrogen sources and one or more minerals in addition to the racemate 2,3-dichloro-1-propanol. The amount of the racemate 2,3-dichloro-1-propanol in the culture medium can be properly selected, and is, for example, preferably about 0.1 to about 0.6% by volume. Examples of such other carbon sources carbohydrates such as glucose, sucrose and glycerol, organic acids such as citric acid, maleic cid and malic acid, and salts of such organic acids. Examples of the nitrogen sources include inorganic nitrogen sources such as ammonium sulfate, ammonium chloride, ammonium nitrate and ammonium phosphate, and organic nitrogen sources such as urea, peptone, casein, yeast extracts and meat extracts. Examples of the minerals includes phosphates, magnesium salts, potassium salts, manganese salts, iron salts, zinc salts and copper salts.

In the practice of the process of this invention, there can be used well grown microbial cells obtained by cultivating the S-(-)-2,3-dichloro-1-propanol-assimilating strain belonging to the genus Alcaligenes in a synthetic medium containing racemate 2,3-dichloro-1-propanol as a carbon source, inorganic nitrogen (e.g., an ammonium salt or a nitrate) as a nitrogen source and inorganic salts, or in an ordinary nutrient medium containing organic nutrient sources and inorganic nutrient sources such as a bouillon medium or a sugar-containing bouillon medium. The use of such well grown cells is preferred.

Preferably, the cultivation of the S-(-)- 2,3-dichloro-1-propanol-assimilating strain of the genus Alcaligenes in the aforesaid medium in the process of this invention is carried out under aerobic conditions. Aerobic cultivating means such as shaking culture and aeration agitation culture may be used for this purpose. The cultivation may be carried out at a temperature of, for example, about 20° to about 45° C., preferably about 25° to about 37° C., and a pH of, for example, about 5 to about 9, preferably about 6.0 to about 7.5. The cultivation time may properly be selected, and is, for example, about 0.5 to about 10 days.

After the cultivation, the optical isomer R-(+)-2,3-dichloro-1-propanol may be recovered from the culture broth. This can be effected, for example, by separating the culture broth into microbial cells and the supernatant by means of a suitable solid-liquid separating procedure such as centrifugal separation, and separating R-(+)-2,3-dichloro-1-propanol in the supernatant by treatment with a charcoal column, extraction with ether, distillation under reduced pressure, etc.

In the practice of the process of this invention, the S-(-)-2,3-dichloro-1-propanol-assimilating strain belonging to the genus Alcaligenes may be used in an immobilized form fixed to an inert substrate. Means of fixation are known per se and can be utilized in this invention. For example, living cells of the strain may be fixed by using such a substrate as acrylamide, kappacarrageenan, agar, gelatin or sodium alginate. After fixation, the cells may be crushed into a suitable size and shape, and used in the process of this invention. The use of immobilized cells has the advantage that the operation of separating the supernatant and the cells from the culture broth after the cultivation becomes easy, and the immobilized cells may be repeatedly used.

According to this invention, there is also provided a process for producing optically active S-(+)-epichlorohydrin, which comprises reacting the optical isomer R-(+)-2,3-dichloro-1-propanol obtained as above with an alkali. This process can be carried out by contacting R-(+)-2,3-dichloro-1-propanol with the alkali in an aqueous medium. The reaction temperature may, for example, be about 0° C. to room temperature (for example, about 30° C.). Examples of the alkali are alkali metal hydroxides and alkali metal alcoholates. Specific examples of the alkali are sodium hydroxide, potassium hydroxide, lithium hydroxide, sodium methylate and sodium ethylate.

BRIEF DESCRIPTION OF THE DRAWING

In FIG. 1, the solid line shows the commercially available β-DCH and the dotted line shows R-(+)-β-DCH.

EXAMPLES

Figure 1:
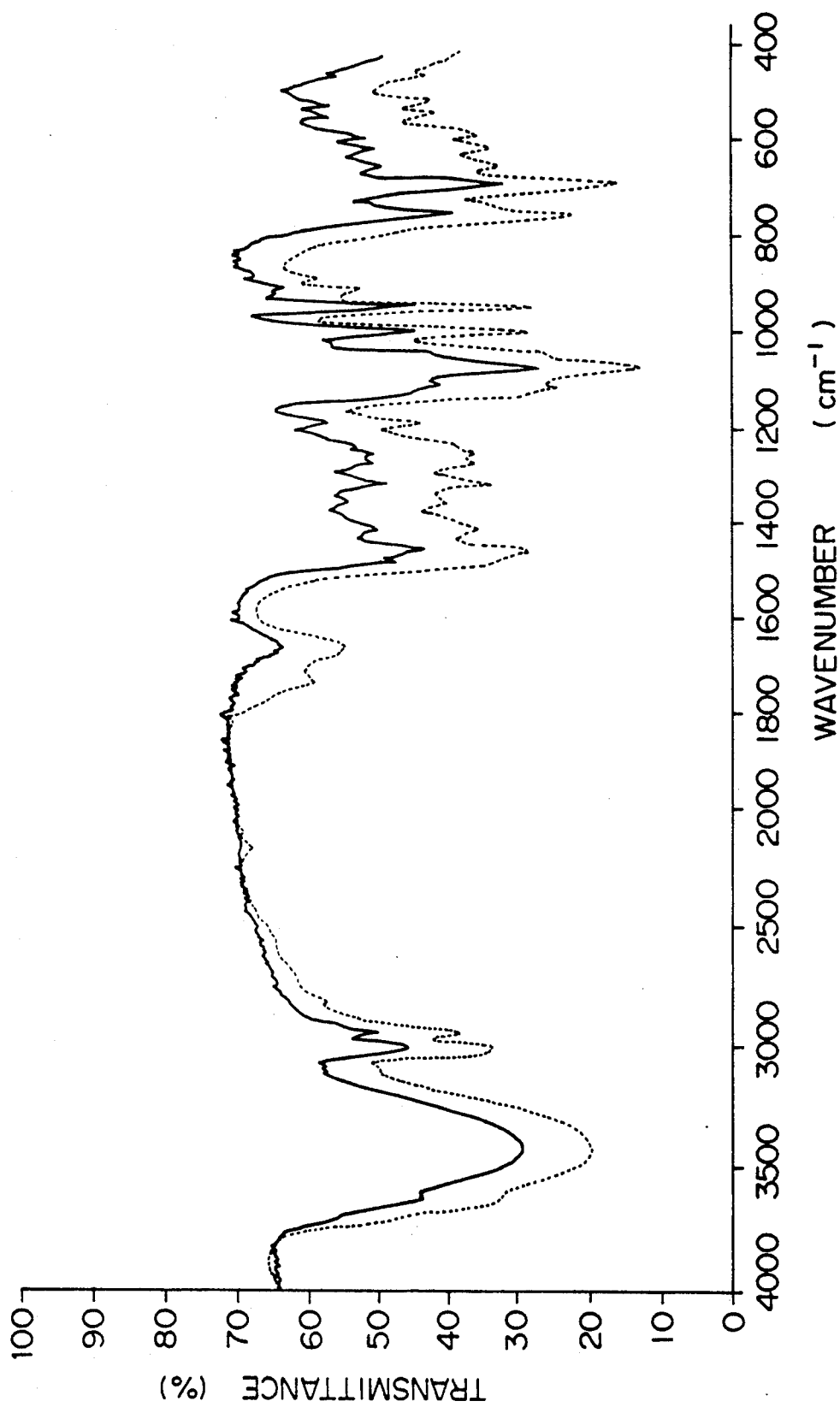
FIG. 1 shows infrared absorption spectra of R-(+)-2,3-dichloro-1-propanol obtained in Example 1 of the invention and a commercially available substance identical to it.

The following examples illustrate the present invention in more detail.

In the following examples, all percentages are by weight unless otherwise specified, and β-DCH stands for 2,3-dichloro-1-propanol.

EXAMPLE 1

Twenty liters of a medium of 1.0% of yeast extract, 2.0% of glycerol and 1.0% of polypeptone, pH 7.0 was poured into a 30-liter jar fermentor, and, after sterilization with heating in a usual manner, Alcaligenes DS-K-S38 (FERM BP-3101) was inoculated and cultivated for 24 hours under the following conditions:

| Temperature | 30° C. |
|---|---|
| pH | Initial pH 7.0 |
| Aeration volume | 20 liters/min. |
| Stirring revolution number | 300 r.p.m. |

After completion of the cultivation, the microbial cells and the culture filtrate were separated using a centrifuge to obtain 600 g of intact cells. The intact cells were then suspended in the following synthetic medium to make the volume 10 liters, and immobilized with acrylamide in a usual manner. The immobilized product was disrupted with a mixer into a size of 0.5 to 1 mm square and sufficiently washed with the synthetic medium.

Components of Synthetic Medium

| Ammonium sulfate | 0.05 wt. % |
|---|---|
| Ammonium nitrate | 0.05 wt. % |
| Dipotassium hydrogenphosphate | 0.1 wt. % |
| Sodium dihydrogenphosphate | 0.2 wt. % |
| Disodium hydrogenphosphate | 0.1 wt. % |

-continued

| Magnesium sulfate | 0.05 wt. % |
|---|---|
| Iron sulfate, copper sulfate and manganese sulfate | trace |
| pH | pH 6.8 |

The thus prepared immobilized product was then placed in a 100-liter jar fermentor and the synthetic medium was added thereto to make the whole volume 80 liters. Then, 320 ml of racemate -DCH and 160 g of calcium carbonate were added, and the mixture was stirred under the following conditions:

| Temperature | 30° C. |
|---|---|
| Aeration volume | 40 liters/min. |
| Revolution number | 300 r.p.m. |

72 Hours after the start of the reaction, the supernatant and the immobilized product were separated by filtration, and the remaining (-DCH was isolated from the filtrate by an active carbon column, ether extraction and vacuum distillation to obtain 152 g. Identification of this substance was carried out according to the following methods.

1) Identification by Gas Chromatography

The present substance was compared with a commercially available β-DCH using a column carrier PEG-20MP, 5%, 60–80 mesh. As a result, their retention times were utterly identical. Chemical purity 98.2% or more.

2) Identification by IR (Infrared Absorption Spectrum)

The absorption pattern of the present substance was utterly identical with that of the commercially available β-DCH, as is shown in the chart of FIG. 1.

From the above, it was clearly revealed that the present substance is β-DCH. Further, it was ascertained by the following method that the present substance is R-(+)-β-DCH.

1) Measurement of Specific Rotation

Specific rotation of the commercially available β-DCH and the present substance are as follows.

The commercially available β-DCH
$[\alpha]_D^{20} = 0.0°$ C. = 1, dichloromethane
The present substance
$[\alpha]_D^{20} = +10.4°$ C. = 1, dichloromethane 2) Preparation of a R-(+)-α-Methoxy-α-Trifluoromethylphenylacetate Ester of Product and Its Analysis by High Performance Liquid Chromatography R-(+)-α-methoxy-α-trifluoromethylphenylacetyl chloride was reacted with commercially available α-DCH or the present substance to prepare its ester derivative, and each product was analyzed by liquid chromatography. The results are shown below.

Analytical Conditions

| Column carrier | |
|---|---|
| ZORBA × ODS (produced by | 4.6 mm × 25 cm |

-continued

| Column carrier | |
|---|---|
| E. I. du Pont Co.) | |
| Eluent | methanol:water = 65:35 (v/v) |
| Elution amount | 1 ml/min. |
| Detection method | absorbance at 260 nm |

Analytical Result

The commercially available β-DCH gave two peaks at 50.5 minutes and 52.0 minutes of the retention time having the same area.

The present substance gave a peak only at 52.0 minutes of the retention time and did not gave any peak at 50.5 minutes.

3) Preparation of Dichloropropyl-N-Phenyl Carbamate and Its Specific Rotation

The commercially available β-DCH or the present substance (each 1 g) and 0.9 g of phenyl isocyanate were added to 30 ml of dried acetone and 0.3 ml of triethylamine, and the mixture was refluxed with heating for about 3 hours, and the resultant dichloropropyl-N-phenyl carbamate was measured for specific rotation.

Analytical Result

The commercially available β-DCH
$[\alpha]_D^{25} = 0.0°$ C. = 1. methanol
The present substance
$[\alpha]_D^{25} = +16.4°$ C. = 1. methanol From the above results, it was revealed that the present substance was R-(+)-β-DCH and its optical purity was 99% or more.

EXAMPLE 2

As in Example 1, 2 liters of a medium of 1.0% of yeast extract, 1.0% polypeptone and 2.0% glycerol, pH 7.0 was poured into a 5-liter jar fermentor, and, according to the conventional manner, after sterilization with heating, DS-K-S38 strain was inoculated and cultivated for 24 hours under the same conditions as in Example 1.

Then, 80 liters of the synthetic medium shown in Example 1, 160 g of calcium carbonate, 320 ml of racemate β-DCH and 40 g of polypeptone were placed in a 100-liter jar fermentor, and, after sterilization with heating, the above culture product was, according to a uaual manner, inoculated therein and cultivated under conditions of a temperature of 30° C., an aeration amount of 40 liters/min and a revolution number of 300 rpm to carry out reaction.

48 Hours after the start of the reaction, the reaction mixture was separated into the supernatant, the cells and the precipitate by a centrifuge, and the remaining β-DCH was fractionated from the supernatant in the same manner as in Example 1 to obtain 148 g of R-(+)-β-DCH.

The specific rotation of the obtained R-(+)-β-DCH was $[\alpha]_D^{20} = +10.4°$ (C=1, dichloromethane), and, as a result of analysis in the same manner as in Example 1, its optical purity was 99% or more.

EXAMPLE 3

100 g of R-(+)-β-DCH obtained in Example 1 was mixed with 650 ml of a 1.4 N aqueous sodium hydroxide solution in a 1000-ml flask, and the mixture was stirred vigorously at room temperature for 80 minutes. Then, 200 ml of ether was added, and, after stirring, the etheral layer was separated. The etheral layer was dried over with magnesium sulfate, distilled to remove the ether, and further distilled to obtain 60.3 g of epichlorohydrin. Measurement by gas chromatography revealed that the purity of this epichlorohydrin was 99.4% or more. Further, its specific rotation was as follows:

$[\alpha]_D^{22} = +34.3°$ (C=3.4, methanol)

Namely, the obtained epichlorohydrin was S-(+)-epichlorohydrin, and its optical purity was 99% or more.

EXAMPLE 4

100 g of R-(+)-(-DCH obtained in Example 2 was treated under the same condition as in Example 3 to obtain 53.2 g of S-(+)-epichlorohydrin. Its specific rotation $[\alpha]_D^{22}$ was +34.3° (C=3.4, methanol), and its optical purity was 99% or more. [Effect of the Invention]

According to the invention, there can be obtained optically active R-(+)-2,3-dichloro-1-propanol, conveniently and in a high purity, from racemate 2,3-dichloro-1-propanol using a bacterium which was separated from the soil and belongs to the genus Alcaligenes.

Further, highly pure optically active S-(+)-epichlorohydrin can be obtained from the obtained R-(+)-2,3-dichloro-1-propanol.

I claim:

1. A process for producing optically active R-(+)-2,3-dichloro-1-propanol, which comprises cultivating S-(+)-2,3-dichloro-1-propanol-assimilating strain DS-K-S38 (FERM BP-3101) in a culture medium containing racemate 2,3-dichloro-1-propanol, and recovering optical isomer R-(+)-2,3-dichloro-1-propanol from the culture broth, said DS-K-S38 strain deposited with the Fermentation Research Institute Agency of Industrial Science and Technology, Japan, under Deposit No. FERM BP-3101.

2. The process of claim 1 wherein the strain is in an immobilized form.

3. The process of claim 1 wherein the cultivation is carried out under aerobic conditions.

4. The process of claim 1 wherein the cultivation is carried out at a temperature of about 20° to about 45° C.

5. The process of claim 1 wherein the cultivation is carried out at a pH of about 5 to about 9.

6. The process of claim 1 wherein the culture medium further contains at least one carbon source, at least one nitrogen source and at least one mineral.

7. A process for producing optically active S-(+)-epichlorohydrin, which comprises cultivating an S-(-)-2,3-dichloro-1-propanol-assimilating strain DS-K-S38 (FERM BP-3101) in a culture medium containing racemate 2,3-dichloro-1-propanol, and recovering optical isomer R-(+)-2,3-dichloro-1-propanol, and reacting said optical isomer with an alkali, said DS-K-S38 strain deposited with the Fermentation Research Institute, Agency of Industrial Science and Technology, Japan, under Deposit No. FERM BP-3101.

8. The process of claim 7 wherein the alkali is an alkali metal hydroxide or an alkali metal alcoholate.

9. The process of claim 7 wherein the strain is in an immobilized form.

10. The process of claim 7 wherein the cultivation is carried out under aerobic conditions.

11. The process of claim 7 wherein the cultivation is carried out at a temperature of about 20° to about 45° C.

12. The process of claim 7 wherein the cultivation is carried out at pH of about 5 to about 9.

13. The process of claim 1 wherein the culture medium further contains at least one carbon source, at least one nitrogen source and at least one mineral.

* * * * *